United States Patent [19]
Haack

[11] Patent Number: 5,114,821
[45] Date of Patent: May 19, 1992

[54] TONER AND DEVELOPER COMPOSITIONS WITH CHARGE ENHANCING ADDITIVES

[75] Inventor: John L. Haack, Pittsford, N.Y.

[73] Assignee: Xerox Corporation, Stamford, Conn.

[21] Appl. No.: 547,001

[22] Filed: Jul. 2, 1990

[51] Int. Cl.$^5$ .................. C03G 9/00; C03G 9/083; C03G 9/107
[52] U.S. Cl. .................. 430/110; 430/106.6
[58] Field of Search .................. 430/106.6, 109, 110

[56] References Cited

U.S. PATENT DOCUMENTS

| | | | |
|---|---|---|---|
| Re. 32,883 | 3/1989 | Lu | 430/110 |
| 3,893,935 | 7/1975 | Jadwin et al. | 252/62.1 |
| 4,221,856 | 9/1980 | Lu | 430/110 |
| 4,323,634 | 4/1982 | Jadwin | 430/110 |
| 4,326,019 | 4/1982 | Lu et al. | 430/108 |
| 4,338,390 | 7/1982 | Lu | 430/106 |
| 4,490,455 | 12/1984 | Hoffend et al. | 430/110 |
| 4,513,075 | 4/1985 | Narusawa et al. | 430/109 |
| 4,604,338 | 8/1982 | Gruber et al. | 430/106 |
| 4,684,596 | 8/1987 | Bonser et al. | 430/110 |
| 4,752,550 | 6/1988 | Barbetta et al. | 430/106.6 |
| 4,792,513 | 12/1988 | Gruber et al. | 430/110 |
| 4,812,381 | 3/1989 | Burger et al. | 430/110 |
| 4,826,749 | 5/1989 | Kawagishi et al. | 430/110 |
| 4,834,921 | 5/1989 | Eugner et al. | 260/501.15 |
| 4,904,762 | 2/1990 | Chang et al. | 430/110 |

FOREIGN PATENT DOCUMENTS 1559322  3/1968  France .................. 502/114

*Primary Examiner*—Marion E. McCamish
*Assistant Examiner*—Stephen Crossan
*Attorney, Agent, or Firm*—E. O. Palazzo

[57] ABSTRACT

A toner composition comprised of resin particles, pigment particles, and a quaternary ammonium hydrogen bisulfate charge enhancing additive.

36 Claims, No Drawings

TONER AND DEVELOPER COMPOSITIONS WITH CHARGE ENHANCING ADDITIVES

BACKGROUND OF THE INVENTION

The invention is generally directed to toner and developer compositions, and more specifically, the present invention is directed to developer and toner compositions containing charge enhancing additives, which impart or assist in imparting a positive charge to the toner resin particles and can enable toners with rapid admix characteristics. In one embodiment, there are provided in accordance with the present invention toner compositions comprised of resin particles, pigment particles, and quaternary ammonium hydrogen bisulfates, including distearyl methyl hydrogen ammonium bisulfate. In one embodiment, the present invention is directed to toners with charge additives of tetraalkylammonium sulfonates such as dimethyl distearyl ammonium alkyl or perfluoralkyl sulfonates. The aforementioned additives in embodiments of the present invention enable, for example, toners with rapid admix of less than about 15 seconds, extended developer life, stable electrical properties, high image print quality with substantially no background deposits, and compatibility with fuser rolls including Viton fuser rolls. Also, the aforementioned toner compositions usually contain pigment particles comprised of, for example, carbon black, magnetites, or mixtures thereof, cyan, magenta, yellow, blue, green, red, or brown components, or mixtures thereof thereby providing for the development and generation of black and/or colored images. The toner compositions of the present invention in embodiments thereof possess excellent admix characteristics as indicated herein, and maintain their triboelectric charging characteristics for an extended number of imaging cycles exceeding, for example, 1,000,000 in a number of embodiments. The toner and developer compositions of the present invention can be selected for electrophotographic, especially xerographic, imaging and printing processes, including color processes.

Developer compositions with charge enhancing additives, which impart a positive charge to the toner resin, are known. Thus, for example, there is described in U.S. Pat. No. 3,893,935 the use of quaternary ammonium salts as charge control agents for electrostatic toner compositions. In this patent, there are disclosed quaternary ammonium compounds with four R substituents on the nitrogen atom, which substituents represent an aliphatic hydrocarbon group having 7 or less, and preferably about 3 to about 7 carbon atoms, including straight and branch chain aliphatic hydrocarbon atoms, and wherein X represents an anionic function including, according to this patent, a variety of conventional anionic moieties such as halides, phosphates, acetates, nitrates, benzoates, methylsulfates, perchloride, tetrafluoroborate, benzene sulfonate, and the like. U.S. Pat. No. 4,221,856 which discloses electrophotographic toners containing resin compatible quaternary ammonium compounds in which at least two R radicals are hydrocarbons having from 8 to about 22 carbon atoms, each other R is a hydrogen or hydrocarbon radical with from 1 to about 8 carbon atoms, and A is an anion, for example, sulfate, sulfonate, nitrate, borate, chlorate, and the halogens such as iodide, chloride and bromide, reference the Abstract of the Disclosure and column 3; a similar teaching is presented in U.S. Pat. No. 4,312,933 which is a division of U.S. Pat. No. 4,291,111; and similar teachings are presented in U.S. Pat. No. 4,291,112 wherein A is an anion including, for example, sulfate, sulfonate, nitrate, borate, chlorate, and the halogens. There are also described in U.S. Pat. No. 2,986,521 reversal developer compositions comprised of toner resin particles coated with finely divided colloidal silica. According to the disclosure of this patent, the development of electrostatic latent images on negatively charged surfaces is accomplished by applying a developer composition having a positively charged triboelectric relationship with respect to the colloidal silica.

Also, there are disclosed in U.S. Pat. No. 4,338,390, the disclosure of which is totally incorporated herein by reference, developer compositions containing as charge enhancing additives organic sulfate and sulfonates, which additives can impart a positive charge to the toner composition. Further, there are disclosed in U.S. Pat. No. 4,298,672, the disclosure of which is totally incorporated herein by reference, positively charged toner compositions with resin particles and pigment particles, and as charge enhancing additives alkyl pyridinium compounds. Additionally, other documents disclosing positively charged toner compositions with charge control additives include U.S. Pat. Nos. 3,944,493; 4,007,293; 4,079,014; 4,394,430 and 4,560,635 which illustrate a toner with a disteary dimethyl ammonium methyl sulfate charge additive. One disadvantage that may be associated with the charge additive of the '635 patent resides in its apparent inherent instability in some instances as the additive may thermally and chemically degrade, and react with other toner components.

The following prior art, all United States patents, were listed in a patentability search report letter: U.S. Pat. No. 4,812,381 which discloses toners and developers containing charge control agents comprising quaternary ammonium salts of the formula indicated, for example, in the Abstract of the Disclosure, wherein R is alkyl with from 12 to 18 carbon atoms, and the anion is a trifluoromethyl sulfonate; also note, for example, the information presented in columns 2 and 3 of this patent; a similar teaching is presented in U.S. Pat. No. 4,834,921; U.S. Pat. No. 4,490,455 which discloses toners with, for example, amine salt charge enhancing additives, reference the Abstract of the Disclosure for example, and wherein A is an anion including those derived from aromatic substituted sulfonic acids, such as benzene sulfonic acid, and the like, see column 3, beginning at line 33; U.S. Pat. No. 4,221,856 directed to toners with a quaternary ammonium compound wherein A is an anion such as sulfate, sulfonate, nitrate, borate, chlorate, and certain halogens, see the Abstract of the Disclosure; U.S. Pat. No. Re. 32,883 (a reissue of U.S. Pat. No. Re. 4,338,390) illustrates toners with sulfate and sulfonate charge additives, see the Abstract of the Disclosure, wherein $R_4$ is an alkylene, and the anion contains a $R_5$ which is a tolyl group, or an alkyl group of from 1 to 3 carbon atoms, and n is the number 3; U.S. Pat. No. 4,323,634 which discloses toners with charge additives of the formulas presented in colum 3, wherein at least one of the R's is a long chain amido group, and X is a halide ion or an organosulfur containing group; U.S. Pat. No. 4,326,019 relating to toners with long chain hydrazinium compounds, wherein the anion A can be a sulfate, sulfonate, phosphate, halides, nitrate, see the Abstract of the Disclosure for example; U.S. Pat. No. 4,752,550 which illustrates toners with inner salt charge additives or mixtures of charge additives, see for example column 8; U.S. Pat. No. 4,684,596 which discloses toners with charge additives of the formula provided in column 3 wherein X can be a variety of anions such as trifluoromethane sulfonate, and U.S. Pat. Nos. 4,604,338; 4,792,513; 3,893,935; 4,826,749, and 4,604,338, the disclosure of each of the aforementioned patents being totally incorporated herein by reference.

The following prior art, all U.S. patents, is mentioned: U.S. Pat. No. 4,812,381 relating to toners and developers with quaternary ammonium salts of the formula illustrated in column 3, the preparation thereof, see column 4, and also note the working Examples, columns 7 and 8, wherein specific charge additives, such as octadecyl ammonium trifluoromethane sulfonate, are reported; U.S. Pat. No. 4,675,118 which discloses certain quaternary salts as fabric softeners, see the Abstract of the Disclosure, and note column 1, for example, wherein X is as recited including $OSO_3CH_3$ and halide; U.S. Pat. No. 4,752,550, the disclosure of which is totally incorporated herein by reference, directed to toners and developers with inner salt charge additives and mixtures of such salts with other charge additives, see for example column 4; Reissue 32,883 (a reissue of U.S. Pat. No. 4,338,390), the disclosures of which are totally incorporated herein by reference, wherein toners with organic sulfonate and organic sulfate charge enhancing additives are illustrated, see columns 3, 4, and 5 to 10 for example; and U.S. Pat. No. 4,058,585 which discloses a process of extracting metals with organic solvent solutions of the salts of hydrogen ionic exchange agents, and quaternary ammonium compounds. Processes for preparing quaternary ammonium salts by an ion exchange or ion pair extraction method with soluble quaternary compounds is known, reference for example Phase Transfer Catalysis, Principles and Techniques, Academic Press, N.Y., 1978, especially page 76, C.M. Starks, and C. Liotta, the disclosure of this textbook being totally incorporated herein by reference, and "Preparative Ion Pair Extraction", Apotekarsocieteten/Hassle, Lakemidel, pages 139 to 148, Sweden, 1974, the disclosure of which is totally incorporated herein by reference, which illustrates the preparation of certain bisulfates with water soluble ammonium salt reactants and a two-phase method wherein the product resides in the water phase.

Moreover, toner compositions with negative charge enhancing additives are known, reference for example U.S. Pat. Nos. 4,411,974 and 4,206,064, the disclosures of which are totally incorporated herein by reference. The '974 patent discloses negatively charged toner compositions comprised of resin particles, pigment particles, and as a charge enhancing additive ortho-halo phenyl carboxylic acids. Similarly, there are disclosed in the '064 patent toner compositions with chromium, cobalt, and nickel complexes of salicylic acid as negative charge enhancing additives.

There is illustrated in U.S. Pat. Nos. 4,404,271 a complex system for developing electrostatic images with a toner which contains a metal complex represented by the formula in column 2, for example, and wherein ME can be chromium, cobalt or iron. Additionally, other patents disclosing various metal containing azo dyestuff structures wherein the metal is chromium or cobalt include U.S. Pat. Nos. 2,891,939; 2,871,233; 2,891,938; 2,933,489; 4,053,462 and 4,314,937. Also, in U.S. Pat. No. 4,433,040, the disclosure of which is totally incorporated herein by reference, there are illustrated toner compositions with chromium and cobalt complexes of azo dyes as negative charge enhancing additives.

Illustrated in U.S. Pat. No. 4,937,157, the disclosure of which is totally incorporated herein by reference, are toner compositions comprised of resin, pigment or dye, and tetraalkyl, wherein alkyl, for example, contains from 1 to about 30 carbon atoms, ammonium bisulfate charge enhancing additives such as distearyl dimethyl ammonium bisulfate, tetramethyl ammonium bisulfate, tetraethyl ammonium bisulfate, tetrabutyl ammonium bisulfate, and preferably dimethyl dialkyl ammonium bisulfate compounds where the dialkyl radicals contain from about 10 to about 30 carbon atoms, and more preferably dialkyl radicals with from about 14 to about 22 carbon atoms, and the like. The aforementioned charge additives can be incorporated into the toner or may be present on the toner surface. Advantages of rapid admix, appropriate triboelectric characteristics, and the like are achieved with many of the toners of the aforementioned '157 patent. Advantages of the charge additives of the present invention in embodiments thereof over the additives of the aforementioned '157 patent include improved stable toner admix rate performance; with the quaternary ammonium hydrogen bisulfate salts economical methods for the preparation thereof and purification thereof by a single process step; with the tetraalkyl ammonim alkyl or perfluoroalkyl sulfonates usually more acceptable thermal stability and excellent chemical stability with respect to solvolysis permitting improved shelf stability of, for example, the toner charge enhancing properties, and the like.

Quaternary ammonium bisulfates disclosed in the aforementioned '157 patent can be of the formula $R'_2R''_2N^+X^-$, wherein R' is aryl, substituted aryl such as alkylaryl, alkyl, preferably with 1 to about 30 carbon atoms, such as methyl, ethyl, propyl, butyl, hexyl, heptyl, and preferably dimethyl dialkyl ammonium bisulfate compounds where the dialkyl radicals are from about 10 to about 30 carbon atoms, and more preferably dialkyl radicals with from about 14 to about 22 carbon atoms; R" is aryl, substituted aryl such as alkylaryl, alkyl, preferably containing from 1 to about 18 carbon atoms; and $X^-$ is a bisulfate ($HSO_4$) anion. These charge control additives may be prepared by ionic exchange reactions from a variety of tetrasubstituted ammonium salts, especially those of the formula $R'_2R''_2N^+X^-$ where $X^-$ is selected from the group consisting of halide, alkyl or aryl sulfate, alkoxide, hydroxide, acetate, benzoate and phosphate; and R' and R" are as defined herein. The tetrasubstituted ammonium salt selected can be heated in an appropriate solvent or solvents, such as water, in the presence of a stoichiometric amount of sulfuric acid. One typical process of preparation involves heating at an effective temperature of, for example, from about 40° to about 100° C. for an appropriate period of time, such as from about 5 to about 15 hours, the insoluble tetrasubstituted ammonium chloride or other halide, such as distearyl dimethyl ammonium choride (DDACl), or the corresponding methyl sulfate salt, distearyl dimethyl ammonium methyl sulfate (DDAMS) in aqueous solution, about one molar equivalent in 85 molar equivalents of water and 10 molar equivalents of sulfuric acid in 56 molar equivalents of water. The crude product resulting after cooling to room temperature can be collected by filtration, and then purified by washing with various solvents such as acetone, followed by recrystallization from, for example, an appropriate solvent such as acetone or methanol, and the like. The resulting products can be identified by a number of techniques including melting point information, differential scanning calorimetry, infrared spectra, carbon, and proton nuclear magnetic resonance, ion chromotography, elemental analysis, and the like.

Processes for the preparation of quaternary ammonium bisulfate charge enhancing additives are illustrated in copending application U.S. Ser. No. 396,497 entitled "Quaternary Ammonium Compounds and Processes Thereof", with the listed inventor John L. Haack, the disclosure of which is totally incorporated herein by reference. Also, toner compositions comprised of a mixture of charge enhancing additives wherein one of the additives can be the above bisulfate and processes thereof are illustrated in U.S. Pat. No. 4,904,762, the disclosure of which is totally incorporated herein by reference.

Process embodiments illustrated in the aforementioned copending application and U.S. patent for the preparation of the bisulfate charge additives include the reaction of water insoluble quaternary ammonium salts, such as distearyl dimethyl ammonium methyl sulfate; distearyl dialkyl ammonium halides, such as distearyl dimethyl ammonium halide, especially the chloride or bromide; dialkyl distearyl ammonium hydroxides, wherein alkyl contains from 10 to about 30 carbon atoms, such as dimethyl distearyl ammonium hydroxide, and diethyl distearyl ammonium hydroxide; distearyl ammonium tosylate, such as dimethyl distearyl ammonium tosylate; distearyl dialkyl, wherein alkyl, for example, contains from 1 to about 30 carbon atoms; ammonium alkyl, wherein alkyl, for example, contains from 1 to about 20 carbon atoms; sulfonate; and the like with a sulfuric acid in the presence of heat. Usually a solvent for the acid, such as water, is selected. The acid is selected in effective amounts of, for example, from about 1 to about 10 molar equivalents, and preferably from about 5 to about 8 molar equivalents to about 1 molar equivalent of the quaternary ammonium salt reactant. Heating of the reaction mixture can be accomplished at various temperatures depending, for example, on the reactants selected, preferably the reaction, however, is accomplished at a temperature of from about 40° to about 100° C. Distearyl dimethyl ammonium methyl sulfate can be heated in an appropriate solvent or solvent mixture in the presence of stoichiometric amount of sulfuric acid. The solvent system comprised, for example, of water, water and alcohol mixtures, water and tetrahydrofuran mixtures, water and acetone mixtures, and water and halogenated, especially chlorinated, solvent mixtures may be selected permitting a single phase or two phase system to facilitate the speed thereof by, for example, from days to hours of the reaction and enabling the isolation and purification of the desired quaternary ammonium product. In the one phase method, for example, there is dissolved the DDAMS quaternary ammonium salt reactant and the concentrated sulfuric acid, water, a water miscible organic cosolvent including acetone, dioxane, glycol ethers, tetrahydrofuran, or an aqueous alcohol, preferably methanol or tetrahydrofuran. Thereafter, the resulting solution can be heated, followed by cooling whereby a precipitate of the desired bisulfate product is obtained subsequent to isolation by filtration. The product may be purified by, for example, known recrystallization methods. With a two-phase process, the appropriate quaternary ammonium salt in a solvent such as methylene chloride or chloroform is mixed and heated with an aqueous sulfuric acid solution. One preferred two-phase method comprises heating the appropriate powdered DDAMS quaternary ammonium salt reactant in suspension with excess aqueous sulfuric acid. In the aforementioned two-phase methods, the desired bisulfate product can be isolated directly by filtration, and thereafter purified by recrystallization, or other similar methods when desirable. The resulting products obtained with the process of the present invention can be identified by a number of techniques including melting point information, differential scanning calorimetry, infrared spectra, carbon, and proton nuclear magnetic resonance, ion chromotography, elemental analysis, and the like.

Although many charge enhancing additives are known, there continues to be a need for toners with additives, which toners possess many of the advantages illustrated herein. Additionally, there is a need for positive charge enhancing additives which are useful for incorporation into black and/or colored toner compositions. Moreover, there is a need for colored toner compositions containing certain charge enhancing additives. There is also a need for toner compositions with certain charge enhancing additives, which toners in embodiments thereof possess acceptable substantially stable triboelectric charging characteristics, and excellent admixing properties. Moreover, there continues to be a need for positively charged toner and developer compositions. Further, there is a need for toners with certain charge enhancing additives which can be easily and permanently dispersed into toner resin particles. There also is a need for positively charged black, and colored toner compositions that are useful for incorporation into various imaging processes, inclusive of color xerography, as illustrated in U.S. Pat. No. 4,078,929, the disclosure of which is totally incorporated herein by reference; laser printers; and additionally a need for toner compositions useful in imaging apparatuses having incorporated therein layered photoresponsive imaging members, such as the members illustrated in U.S. Pat. No. 4,265,990, the disclosure of which is totally incorporated herein by reference. Also, there is a need for toner compositions which have the desired triboelectric charge level, for example, from about 10 to about 40 microcoulombs per gram, and preferably from about 10 to about 25 microcoulombs per gram, and admix charging rates of from about 5 to about 60 seconds, and preferably from about 15 to about 30 seconds, as determined by the charge spectrograph, preferably for example at low concentrations, that is for example less than 1 percent, and preferably less than about 0.5 percent of the charge enhancing additive of the present invention.

SUMMARY OF THE INVENTION

It is an object of the present invention to provide toner and developer compositions with charge enhancing additives.

In another object of the present invention there are provided positively charged toner compositions useful for the development of electrostatic latent images including color images.

In yet another object of the present invention there are provided positively charged toner compositions containing quaternary ammonium hydrogen bisulfate, especially trialkyl ammonium hydrogen bisulfate charge enhancing additives.

In yet another object of the present invention there are provided positively charged toner compositions containing tetraalkyl ammonium sulfonates, such as dimethyl distearyl ammonium sulfonate charge enhancing additives.

Another object of the present invention resides in providing toner compositions with mixtures of charge enhancing additives wherein one of the additives is a quaternary ammonium hydrogen bisulfate, especially trialkyl ammonium hydrogen bisulfate, or a tetraalkyl ammonium sulfonate, such as dimethyl distearyl ammonium sulfonate.

Also, in another object of the present invention there are provided developer compositions with positively charged toner particles, carrier particles, and the enhancing additives illustrated herein, or mixtures of these additives with other known charge enhancing additives.

In yet a further object of the present invention there are provided humidity insensitive, from about, for example, 20 to 80 percent relative humity at temperatures of from 60° to 80° F. as determined in a relative humidity testing chamber, positively charged toner compositions with desirable admix properties of 5 seconds to 60 seconds as determined by the charge spectrograph, and preferably less than 15 seconds for example, and more preferably from about 1 to about 14 seconds, and acceptable triboelectric charging characteristics of from about 10 to about 40 microcoulombs per gram.

Additionally, in a further object of the present invention there are provided positively charged magnetic toner compositions, and positively charged colored toner compositions containing therein, or thereon quaternary ammonium hydrogen bisulfate, especially trialkyl ammonium hydrogen bisulfate charge enhancing additives, or tetraalkyl ammonium sulfonates, such as dimethyl distearyl ammonium sulfonate charge enhancing additives.

Furthermore, in yet another object of the present invention there are provided toner and developer compositions with quaternary ammonium hydrogen bisulfate, especially trialkyl ammonium hydrogen bisulfate charge enhancing additives, or tetraalkyl ammonium sulfonates, such as dimethyl distearyl ammonium sulfonate charge enhancing additives, which compositions are useful in a variety of electrostatic imaging and printing processes, including color xerography, and wherein the admix charging times are less than 60 seconds.

In another object of the present invention that are provided thermally stable charge enhancing additives, that is for example additives which do not decompose at high temperatures, for example, of from about 130° to about 160° C.

Another object of the present invention resides in the formation of toners which will enable the development of images in electrophotographic imaging apparatuses, which images have substantially no background deposits thereon, are substantially smudge proof or smudge resistant, and therefore are of excellent resolution; and further, such toner compositions can be selected for high speed electrophotographic apparatuses, that is those exceeding 70 copies per minute.

In a another object of the present invention there are provided toners with stable shelf life for extended time periods under a variety of environmental conditions, and wherein the toners have narrow charge distributions, rapid charging kinetics, heat aging stability, and the charge enhancing additives thereof are thermally and chemically stable in embodiments of the present invention.

These and other objects of the present invention can be accomplished in embodiments thereof by providing toner compositions comprised of resin particles, pigment particles, and the charge enhancing additives comprised of quaternary ammonium hydrogen bisulfates, or tetra alkyl ammonium sulfonates. More specifically, the present invention in one embodiment is directed to toner compositions comprised of resin, pigment, or dye, and trialkyl, wherein alkyl, for example, contains from 1 to about 30 carbon atoms, hydrogen ammonium bisulfate charge enhancing additives such as distearyl methyl hydrogen ammonium bisulfate, trimethyl hydrogen ammonium bisulfate, triethyl hydrogen ammonium bisulfate, tributyl hydrogen ammonium bisulfate, didodecyl methyl hydrogen ammonium bisulfate, dihexadecyl methyl hydrogen ammonium bisulfate, and preferably distearyl methyl hydrogen ammonium bisulfate in an embodiment of the present invention. Examples of alkyl groups include methyl, ethyl, propyl, butyl, pentyl, hexyl, heptyl, octyl, nonyl, decyl, stearyl, and the like. The aforementioned charge additives can be incorporated into the toner, may be present on the toner surface or may be present on toner surface additives such as colloidal silica particles. Advantages of rapid admix, appropriate triboelectric characteristics, and the like are achieved with many of the aforementioned toners of the present invention. Also, the toners of the present invention may contain mixtures of the aforementioned charge additive with other charge additives such as distearyl dimethyl ammonium methyl sulfate, the bisulfates, and charge additives of the copending application U.S. Ser. No. 396,497 and U.S. Pat. Nos. 4,904,762 and 4,937,157, the disclosures of which are totally incorporated herein by reference, the charge additives of the patents mentioned herein; and the like. With mixtures, from about 0.05 to about 1.0 percent by weight of the charge enhancing additive of the present invention can be selected, and from about 0.05 to about 1.0 percent of a second charge enhancing additive can be selected for the toners in embodiments of the present invention. Other amounts of mixtures may also be selected in embodiments of the present invention.

In another embodiment of the present invention there are provided, subsequent to known micronization and classification, toner particles with an average diameter of from about 10 to about 20 microns comprised of resin particles, pigment particles, and the charge enhancing additives comprised of quaternary ammonium hydrogen bisulfates, tetraalkyl ammonium sulfonates, mixtures thereof, and the like.

In an embodiment, the quaternary hydrogen ammonium bisulfates can be represented by the formula $R'_2N^+R''$ $HX^-$ wherein $R'$ is alkyl with, for example, from 1 to about 25 carbon atoms; $R''$ is alkyl with, for example, from 1 to about 10 carbon atoms; and X is an anion of bisulfate ($HSO_4—$). Alkyl for $R'$ can include substituents with 1 to about 30 carbon atoms, and preferably with 1 to about 20 carbon atoms such as methyl, ethyl, propyl, butyl, hexyl, heptyl, octyl, nonyl, decyl, stearyl, and the like. Alkyl for $R''$ can, for example, include substituents with 1 to about 10 carbon atoms, and preferably with 1 to about 8 carbon atoms such as methyl, ethyl, propyl, butyl, hexyl, heptyl, octyl and the like.

Typical tetralkylammonium sulfonate charge additives include those represented by the following formul $R_2'N+R_2''X-$ wherein R' is alkyl with, for example, from 1 to about 25 carbon atoms; R'' is alkyl with, for example, from 1 to about 10 carbon atoms; and X is an anion derived from a sulfonic acid ($RSO_3-$). Alkyl for R' can include substituents with 1 to about 30 carbon atoms, and preferably with 1 to about 20 carbon atoms such as methyl, ethyl, propyl, butyl, hexyl, heptyl, octyl, nonyl, decyl, stearyl, and the like. Alkyl for R'' can include substituents with 1 to about 10 carbon atoms, and preferably with 1 to about 8 carbon atoms such as methyl, ethyl, propyl, butyl, hexyl, heptyl, octyl and the like. Anion examples include $CH_3SO_3-$, $CF_3SO_3-$, $RSO_3-$, wherein R is alkyl, or perfluoroalkyl that, for example, contains at least two carbon atoms, and the like.

Examples of specific bisulfate charge enhancing additives are trialkyl hydrogen ammonium bisulfate such as distearyl methyl hydrogen ammonium bisulfate, trimethyl hydrogen ammonium bisulfate, triethyl hydrogen ammonium bisulfate, tributyl hydrogen ammonium bisulfate, dioctyl methyl hydrogen ammonium bisulfate, didodecyl methyl hydrogen ammonium bisulfate, dihexadecyl methyl hydrogen ammonium bisulfate, and the like; and preferably in an embodiment distearyl methyl hydrogen ammonium bisulfate. Examples of tetraalkyl ammonium sulfonate charge additives include distearyl dimethyl ammonium methyl sulfonate, trifluoromethyl sulfonate, tetramethyl ammonium methyl sulfonate, tetramethyl ammonium trifluoromethyl sulfonate, tetrabutyl ammonium methyl sulfonate, tetrabutyl ammonium trifluoromethyl sulfonate, dioctyl dimethyl ammonium methyl sulfonate, dioctyl dimethyl ammonium trifluoromethyl sulfonate, didodecyl dimethyl ammonium methyl sulfonate, didodecyl dimethyl ammonium trifluoromethyl sulfonate, dihexadecyl dimethyl ammonium methyl sulfonate, dihexadecyl dimethyl ammonium trifluoromethyl sulfonate, and the like; and preferably distearyl methyl hydrogen ammonium bisulfate or distearyl dimethyl trifluoromethyl sulfonate.

The tetraalkyl ammonium alkyl sulfonates and tetraalkyl ammonium perfluoroalkyl sulfonate charge additives of the present invention may be prepared by ionic exchange reactions from a variety of tetrasubstituted ammonium salts, especially those of the formula $R'_2R''_2N+X-$ where $X-$ is selected from the group consisting of halide, alkyl or aryl sulfate, alkoxide, hydroxide, acetate, benzoate and phosphate; and R' and R'' are as defined herein. The tetrasubstituted ammonium salt selected can be heated in an appropriate solvent or solvents, such as water, in the presence of a stoichiometric, or excess amount of alkyl or perfluoroalkyl sulfonic acid. Another method involves the alkylation of the corresponding tertiary amines with an alkyl sulfonate ester, for example methyl methane sulfonate.

One typical process of preparation involves heating at an effective temperature of, for example, from about 40° to about 100° C. for an appropriate period of time, such as from about 5 to about 15 hours, insoluble tetrasubstituted ammonium chloride or other halide, such as distearyl dimethyl ammonium chloride (DDACl), or the corresponding methyl sulfate salt, distearyl dimethyl ammonium methyl sulfate (DDAMS) in an aqueous solution, about one molar equivalent in about 85 molar equivalents of water and about 10 molar equivalents of alkyl of perfluoroalkyl sulfonic acid in 56 molar equivalents of water. The crude product resulting after cooling to room temperature can be collected by filtration, and then purified by washing with various solvents such as acetone, followed by recrystallization from, for example, an appropriate solvent such as acetone or methanol, and the like. The resulting products can be identified by a number of techniques including melting point information, differential scanning calorimetry, infrared spectra, carbon, proton nuclear magnetic resonance, ion chromatography, elemental analysis, and the like.

Process embodiments illustrated in the aforementioned copending applications and patents with the following exceptions can be selected for the preparation of the alkyl or perfluoroalkyl sulfonate charge additives of the present invention include the reaction of water insoluble quaternary ammonium salts, such as distearyl dimethyl ammonium methyl sulfate; distearyl dialkyl ammonium halides, such as distearyl dimethyl ammonium halide, especially the chloride or bromide; dialkyl distearyl ammonium hydroxides, wherein alkyl contains from 10 to about 30 carbon atoms, such as dimethyl distearyl ammonium hydroxide, and diethyl distearyl ammonium hydroxide; distearyl ammonium tosylate, such as dimethyl distearyl ammonium tosylate; distearyl dialkyl, wherein alkyl, for example, contains from 1 to about 30 carbon atoms; ammonium alkyl, wherein alkyl, for example, contains from 1 to about 20 carbon atoms; sulfonate; and the like with an alkyl, or perfluoroalkyl sulfonic acid in the presence of heat. Usually a solvent for the acid, such as water, is selected. The acid is selected in effective amounts of, for example, from about 1 to about 10 molar equivalents, and preferably from about 5 to about 8 molar equivalents to about 1 molar equivalent of the quaternary ammonium salt reactant. Heating of the reaction mixture can be accomplished at various temperatures depending, for example, on the reactants selected, preferably the reaction, however, is accomplished at a temperature of from about 40° to about 100° C. Distearyl dimethyl ammonium methyl sulfate can be heated in an appropriate solvent or solvent mixture in the presence of stoichiometric amount of a sulfonic acid. The solvent system comprised, for example, of water, water and alcohol mixtures, water and tetrahydrofuran mixtures, water and acetone mixtures, and water and halogenated, especially chlorinated, solvent mixtures may be selected permitting a single phase or two phase system to facilitate the speed thereof by, for example, from days to hours of the reaction and enabling the isolation and purification of the desired quaternary ammonium product. In the one phase method, for example, there is dissolved the DDAMS (distearyl dimethyl ammonium methyl sulfate) quaternary ammonium salt reactant and the sulfonic acid, water, a water miscible organic cosolvent including acetone, dioxane, glycol ethers, tetrahydrofuran, or an aqueous alcohol, preferably methanol or tetrahydrofuran. Thereafter, the resulting solution can be heated, followed by cooling whereby a precipitate of the desired sulfonate product is obtained subsequent to isolation by filteration. The product may be purified by, for example, known recrystallization methods. With a two-phase process, the appropriate quaternary ammonium salt in a solvent, such as methylene chloride or chloroform, is mixed and heated with an aqueous sulfonic acid solution. One preferred two-phase method comprises, as illustrated herein, heating the appropriate powdered DDAMS quaternary ammonium salt reactant in suspension with excess aqueous sulfonic acid. In the aforementioned two-phase methods, the desired sulfonate product can be isolated directly by filtration, and thereafter purified by recrystallization, or other similar methods when desirable. The resulting products obtained with the process of the present invention can be identified by a number of techniques including melting point information, differential scanning calorimetry, infrared spectra, carbon, and proton nuclear magnetic resonance, ion chromotography, elemental analysis, and the like.

A process embodiment comprises the addition of the appropriate insoluble quaternary ammonium salt, such as distearyl dimethyl ammonium methyl sulfate DDAMS, and water, followed by dissolving sulfonic acid in the aforementioned mixture, and thereafter separating the desired sulfonate product therefrom wherein water is selected in a sufficient amount to suspend the quaternary ammonium salt reactant, that is for example for one-half part of water to one part of reactant; the addition of a cosolvent to the water, acid, and DDAMS reactants, which cosolvent includes tetrahydrofuran, aliphatic alcohols, such as methanol, ethanol, propanol, butanol; dioxane, glycol ethers, acetone, and the like; and then separating the desired product from the reaction mixture whereby there is enabled the DDAMS reactant to be substantially more soluble, for example, and thereby enabling a scale up in manufacturing processes in an effective manner wherein the mixture, for example, comprises from 1 part of water to 0.1 part of a second solvent such as acetone, dioxane, glycol ethers, preferably 0.1:1.0 to about 20:10 of second cosolvent to water, tetrahydrofuran, alcohols, and the like; a two-phase system wherein there is formed a first water layer and a second solvent, such as chloroform or toluene layer, thus the DDAMS reactant is dissolved in chloroform and the water layer containing the acid wherein reaction is accomplished at the water interface, and the product is present in the organic phase containing the chloroform or the toluene. Generally, in the aforementioned two-phase reaction from about 1 part of water to 0.1 to 20 parts by weight of the second solvent, such as chloroform or alcohol, is selected. The two-phase system process generally comprises the preparation of quaternary ammonium compounds $R_4N+X-$ wherein a quaternary ammonium salt is dissolved in a water immiscible organic solvent and added to a mixture comprised of an acid and water, thereafter heating whereby a reaction occurs at the interface between the organic solvent layer and the water layer, cooling, separating the organic layer from the water layer, and obtaining the product from the organic layer.

In an embodiment for the preparation of the bisulfate salts of the present invention, the formula $R'_2R''N+H-$ wherein R' and R" are independently selected from the group consisting of alkyl, aryl, and alkylaryl, and $X-$ is the anion, comprises the reaction by heating of water insoluble quaternary ammonium salts with an acid. In another embodiment, a process for the preparation of quaternary ammonium compounds is accomplished wherein a quaternary ammonium salt is dissolved in a water immiscible organic solvent and added to a mixture comprised of an acid and water, thereafter heating whereby a reaction occurs at the interface between the organic solvent layer and the water layer, cooling, separating the organic layer from the water layer, and obtaining the product from the organic layer; and wherein the quaternary salt reactant is preferably distearyl methyl hydrogen ammonium methyl sulfate and the acid is sulfuric acid.

One process embodiment comprises the adding of the appropriate insoluble quaternary ammonium salt, such as distearyl methyl hydrogen ammonium methyl sulfate, a trialkyl amine, or distearyl methyl amine to water, followed by dissolving sulfuric acid in the aforementioned mixture, and thereafter separating the desired bisulfate product therefrom wherein water is selected in a sufficient amount to suspend the quaternary ammonium salt reactant, that is for example for one-half part of water to one part of reactant; the addition of a cosolvent to the water, acid, quaternary salt or amine reactants, which cosolvent includes tetrahydrofuran, aliphatic alcohols, such as methanol, ethanol, propanol, butanol; dioxane, glycol ethers, acetone and the like; and then separating the desired product from the reaction mixture whereby there is enabled the quaternary salt or amine reactant to be substantially more soluble, for example, and thereby enabling a scale up in manufacturing processes in an effective manner wherein the mixture, for example, comprises from 1 part of water to 0.1 part of a second solvent such as acetone, dioxane, glycol ethers, preferably 0.1:1.0 to about 20:10 of second cosolvent to water, tetrahydrofuran, alcohols, and the like; a two-phase system wherein there is formed a first water layer and a second solvent, such as chloroform or toluene layer, thus the quaternary salt or amine reactant is dissolved in chloroform and the water layer containing the acid wherein reaction is accomplished near the water interface, and the product is present in the organic phase containing the chloroform or the toluene. Generally, in the aforementioned two-phase reaction from about 1 part of water to 0.1 to 20 parts by weight of the second solvent, such as chloroform or alcohol, is selected. The two-phase system process generally comprises the preparation of quaternary ammonium compounds $R'_2R''N+HX-$ wherein a quaternary ammonium salt is dissolved in a water immiscible organic solvent and added to a mixture comprised of an acid and water, thereafter heating whereby a reaction occurs near the interface between the organic solvent layer and the water layer, cooling, separating the organic layer from the water layer, and obtaining the product from the organic layer.

The toner compositions of the present invention can be prepared by a number of known methods, such as admixing and heating resin particles such as styrene butadiene copolymers, pigment particles such as magnetite, carbon black, or mixtures thereof, and preferably from about 0.5 percent to about 5 percent of the aforementioned charge enhancing additives, or mixtures of charge additives, in a toner extrusion device, such as the ZSK53 available from Werner Pfleiderer, and removing the formed toner composition from the device. Subsequent to cooling, the toner composition is subjected to grinding utilizing, for example, a Sturtevant micronizer for the purpose of achieving toner particles with a volume median diameter of less than about 25 microns, and preferably of from about 8 to about 12 microns, which diameters are determined by a Coulter Counter. Subsequently, the toner compositions can be classified utilizing, for example, a Donaldson Model B classifier for the purpose of removing fines, that is toner particles less than about 4 microns volume median diameter.

Illustrative examples of suitable toner resins selected for the toner and developer compositions of the present invention include polyamides, polyolefins, styrene acrylates, styrene methacrylates, styrene butadienes, crosslinked styrene polymers, epoxies, polyurethanes, vinyl resins, including homopolymers or copolymers of two or more vinyl monomers; and polymeric esterification products of a dicarboxylic acid and a diol comprising a diphenol. Vinyl monomers include styrene, p-chlorostyrene, saturated mono-olefins such as ethylene, propylene, butylene, isobutylene and the like; unsaturated mono-olefins such as vinyl acetate, vinyl propionate, and vinyl butyrate; vinyl esters like esters of monocarboxylic acids including methyl acrylate, ethyl acrylate, n-butylacrylate, isobutyl acrylate, dodecyl acrylate, n-octyl acrylate, phenyl acrylate, methyl methacrylate, ethyl methacrylate, and butyl methacrylate; acrylonitrile, methacrylonitrile, acrylamide, mixtures thereof; and the like; styrene butadiene copolymers with a styrene content of from about 70 to about 95 weight percent, reference the U.S. patents mentioned herein, the disclosures of which have been totally incorporated herein by reference. In addition, crosslinked resins, including polymers, copolymers, and homopolymers of the aforementioned styrene polymers may be selected.

As one toner resin, there are selected the esterification products of a dicarboxylic acid and a diol comprising a diphenol. These resins are illustrated in U.S. Pat. No. 3,590,000, the disclosure of which is totally incorporated herein by reference. Other specific toner resins include styrene/methacrylate copolymers, and styrene/butadiene copolymers; Pliolites; suspension polymerized styrene butadienes, reference U.S. Pat. No. 4,558,108, the disclosure of which is totally incorporated herein by reference; polyester resins obtained from the reaction of bisphenol A and propylene oxide; followed by the reaction of the resulting product with fumaric acid, and branched polyester resins resulting from the reaction of dimethylterephthalate, 1,3-butanediol, 1,2-propanediol, and pentaerythritol, styrene acrylates, and mixtures thereof. Also, waxes with a molecular weight of from about 1,000 to about 6,000 such as polyethylene, polypropylene, UNILIN ™ hydroxy alcohols and paraffin waxes can be included in, or on the toner compositions as fuser roll release agents.

The resin particles are present in a sufficient, but effective amount, for example from about 70 to about 90 weight percent. Thus, when 1 percent by weight of the charge enhancing additive is present, and 10 percent by weight of pigment or colorant, such as carbon black, is contained therein, about 89 percent by weight of resin is selected. Also, the charge enhancing additive of the present invention may be coated on the pigment particle. When used as a coating, the charge enhancing additive of the present invention is present in an amount of from about 0.1 weight percent to about 5 weight percent, and preferably from about 0.3 weight percent to about 1 weight percent.

Numerous well known suitable pigments or dyes can be selected as the colorant for the toner particles including, for example, carbon black, nigrosine dye, aniline blue, magnetite, or mixtures thereof. The pigment, which is carbon black in an embodiment, should be present in a sufficient amount to render the toner composition highly colored. Generally, the pigment particles are present in amounts of from about 1 percent by weight to about 20 percent by weight, and preferably from about 2 to about 10 weight percent based on the total weight of the toner composition; however, lesser or greater amounts of pigment particles can be selected.

When the pigment particles are comprised of magnetites, thereby enabling single component toners in some instances, which magnetites are a mixture of iron oxides ($FeO \cdot Fe_2O_3$) including those commercially available as Mapico Black, they are present in the toner composition in an amount of from about 10 percent by weight to about 70 percent by weight, and preferably in an amount of from about 10 percent by weight to about 50 percent by weight. Mixtures of carbon black and magnetite with from about 1 to about 15 weight percent of carbon black, and preferably from about 2 to about 6 weight percent of carbon black, and magnetite, such as Mapico Black, in an amount of, for example, from about 5 to about 60, and preferably from about 10 to about 50 weight percent can be selected.

There can also be blended with the toner compositions of the present invention external additive particles including flow aid additives, which additives are usually present on the surface thereof. Examples of these additives include colloidal silicas such as Aerosil, metal salts and metal salts of fatty acids inclusive of zinc stearate, aluminum oxides, cerium oxides, and mixtures thereof, which additives are generally present in an amount of from about 0.1 percent by weight to about 5 percent by weight, and preferably in an amount of from about 0.1 percent by weight to about 1 percent by weight. Several of the aforementioned additives are illustrated in U.S. Pat. Nos. 3,590,000 and 3,800,588, the disclosures of which are totally incorporated herein by reference.

With further respect to the present invention, surface additives such as colloidal silicas such as Aerosil can be surface treated with the charge additives of the present invention illustrated herein in an amount of from about 1 to about 30 weight percent and preferably 10 weight percent, followed by the addition thereof to the toner in an amount of from 0.1 to 10 and preferably 0.1 to 1 weight percent.

There can be included in the toner compositions of the present invention low molecular weight waxes, such as polypropylenes and polyethylenes commercially available from Allied Chemical and Petrolite Corporation, Epolene N-15 commercially available from Eastman Chemical Products, Inc., Viscol 550-P, a low weight average molecular weight polypropylene available from Sanyo Kasei K.K., and similar materials. The commercially available polyethylenes selected have a molecular weight of from about 1,000 to about 1,500, it is believed, while the commercially available polypropylenes utilized for the toner compositions of the present invention are believed to have a molecular weight of from about 4,000 to about 5,000. Many of the polyethylene and polypropylene compositions useful in the present invention are illustrated in British Patent No. 1,442,835, the disclosure of which is totally incorporated herein by reference.

The low molecular weight wax materials are present in the toner composition of the present invention in various amounts, however, generally these waxes are present in the toner composition in an amount of from about 1 percent by weight to about 15 percent by weight, and preferably in an amount of from about 2 percent by weight to about 10 percent by weight.

Encompassed within the scope of the present invention are colored toner and developer compositions comprised of toner resin particles, optional carrier particles, the charge enhancing additives illustrated herein, and as pigments or colorants red, blue, green, brown, magenta, cyan and/or yellow particles, as well as mixtures thereof. More specifically, with regard to the generation of color images utilizing a developer composition with the charge enhancing additives of the present invention, illustrative examples of magenta materials that may be selected as pigments include, for example, 2,9-dimethyl-substituted quinacridone and anthraquinone dye identified in the Color Index as Cl 60710, Cl Dispersed Red 15, diazo dye identified in the Color Index as Cl 26050, Cl Solvent Red 19, and the like. Illustrative examples of cyan materials that may be used as pigments include copper tetra-4-(octadecyl sulfonamido) phthalocyanine, X-copper phthalocyanine pigment listed in the Color Index as Cl 74160, Cl Pigment Blue, and Anthracene Blue, identified in the Color Index as Cl 69810, Special Blue X-2137, and the like; while illustrative examples of yellow pigments that may be selected are diarylide yellow 3,3-dichlorobenzidene acetoacetanilides, a monoazo pigment identified in the Color Index as Cl 12700, Cl Solvent Yellow 16, a nitrophenyl amine sulfonamide identified in the Color Index as Foron Yellow SE/GLN, Cl Dispersed Yellow 33, 2,5-dimethoxy-4-sulfonanilide phenylazo-4'-chloro-2,5-dimethoxy acetoacetanilide, and Permanent Yellow FGL. The aforementioned pigments are incorporated into the toner composition in various suitable effective amounts providing the objectives of the present invention are achieved. In one embodiment, these colored pigment particles are present in the toner composition in an amount of from about 2 percent by weight to about 15 percent by weight calculated on the weight of the toner resin particles.

For the formulation of developer compositions, there are mixed with the toner particles carrier components, particularly those that are capable of triboelectrically assuming an opposite polarity to that of the toner composition. Accordingly, the carrier particles of the present invention can be selected to be of a negative polarity enabling the toner particles, which are positively charged, to adhere to and surround the carrier particles. Illustrative examples of carrier particles include iron powder, steel, nickel, iron, ferrites, including copper zinc ferrites, and the like. Additionally, there can be selected as carrier particles nickel berry carriers as illustrated in U.S. Pat. No. 3,847,604, the disclosure of which is totally incorporated herein by reference. The selected carrier particles can be used with or without a coating, the coating generally containing terpolymers of styrene, methylmethacrylate, and a silane, such as triethoxy silane, reference U.S. Pat. Nos. 3,526,533 and 3,467,634, the disclosures of which are totally incorporated herein by reference; polymethyl methacrylates; other known coatings; and the like. The carrier particles may also include in the coating, which coating can be present in one embodiment in an amount of from about 0.1 to about 3 weight percent, conductive substance, such as carbon black, in an amount of from about 5 to about 30 percent by weight. Polymer coatings not in close proximity in the triboelectric series can also be selected, reference U.S. Pat. Nos. 4,937,166 and 4,935,326, the disclosures of which are totally incorporated herein by reference, including for example Kynar and polymethyl methacrylate mixtures (40/60). Coating weights can vary as indicated herein; generally, however, from about 0.3 to about 2, and preferably from about 0.5 to about 1.5 weight percent coating weight is selected.

Furthermore, the diameter of the carrier particles, preferably spherical in shape, is generally from about 50 microns to about 1,000 microns thereby permitting them to possess sufficient density and inertia to avoid adherence to the electrostatic images during the development process. The carrier component can be mixed with the toner composition in various suitable combinations, however, in an embodiment about 1 to 5 parts per toner to about 100 parts to about 200 parts by weight of carrier are selected.

The toner composition of the present invention can be prepared by a number of known methods including extrusion melt blending the toner resin particles, pigment particles or colorants, the charge enhancing additive and other components as indicated herein, followed by mechanical attrition and classification. Other methods include those well known in the art such as spray drying, melt dispersion, extrusion processing, dispersion polymerization, and suspension polymerization. Also, as indicated herein the toner composition without the charge enhancing additive can be prepared, followed by the addition of surface treated with charge additive colloidal silicas. Further, other methods of preparation for the toner are as illustrated herein.

The toner and developer compositions of the present invention may be selected for use in electrostatographic imaging apparatuses containing therein conventional photoreceptors providing that they are capable of being charged negatively in embodiments thereof. Thus, the toner and developer compositions of the present invention can be used with layered photoreceptors that are capable of being charged negatively, such as those described in U.S. Pat. No. 4,265,990, the disclosure of which is totally incorporated herein by reference. Illustrative examples of inorganic photoreceptors that may be selected for imaging and printing processes include selenium; selenium alloys, such as selenium arsenic, selenium tellurium and the like; halogen doped selenium substances; and halogen doped selenium alloys. Other similar photoreceptors can be selected. Discharge area development may also be selected.

The toner compositions are usually jetted and classified subsequent to preparation to enable toner particles with a preferred average diameter of from about 5 to about 25 microns, and more preferably from about 8 to about 12 microns. Also, the toner compositions of the present invention possess a triboelectric charge of from about 0.1 to about 2 femtocoulombs per micron in embodiments thereof as determined by the known charge spectrograph. Admix time for the toners of the present invention are from about 5 seconds to 1 minute, and more specifically from about 5 to about 15 seconds in embodiments thereof as determined by the known charge spectrograph. These toner compositions with rapid admix characteristics enable, for example, the development of images in electrophotographic imaging apparatuses, which images have substantially no background deposits thereon, even at high toner dispensing rates in some instances, for example exceeding 20 grams per minute; and further, such toner compositions can be selected for high speed electrophotographic apparatuses, that is those exceeding 70 copies per minute.

With further respect to the present invention, one developer composition is comprised of a toner composition containing distearyl methyl hydrogen bisulfate, dimethyl distearyl ammonium methyl sulfonate as a charge enhancing additives, pigment particles such as carbon black, resin particles, and carrier particles comprised of a core containing thereover a plurality and preferably two polymeric coatings, namely a first polymeric coating of, for example Kynar, 40 weight percent, and a second polymeric coating of, for example, polymethacrylate, 60 weight percent, at a total coating weright of 1.25 weight percent, which coatings are not in close proximity in the triboelectric series, reference U.S. Pat. Nos. 4,937,166 and 4,935,326, both entitled "Developer Compositions For Coated Carrier Particles", the disclosures of each of these patents being totally incorporated herein by reference. With the aforementioned carriers, in some embodiments from about 0.1 to about 0.5 weight percent of the charge enhancing additive can be selected. Accordingly, for example, small amounts of charge enhancing additives can be selected for developers with carrier particles containing a double polymeric coating thereover.

With some charge enhancing additives, they may, particularly during heating in the extrusion device, decompose, which disadvantage is avoided with the present invention wherein a bisulfate charge enhancing additive can be incorporated into the toner and during extrusion decomposition thereof is avoided and/or substantially eliminated. Moreover, the charge enhancing additives of the present invention, and in particular the distearyl dimethyl amonium trifluoromethyl sulfonate, are thermally stable at high temperatures as indicated herein as is not the situation with some of the prior art charge enhancing additives.

Also, the toner compositions of the present invention in embodiments thereof possess desirable narrow charge distributions, optimal charging triboelectric values, preferably of from 10 to about 40, and more preferably from about 10 to about 35 microcoulombs per gram with from about 0.1 to about 5 weight percent in one embodiment of the charge enhancing additive; and rapid admix charging times as determined in the charge spectrograph of less than 15 seconds, and more preferably in some embodiments from about 1 to about 14 seconds.

When the charge additives of the present invention are utilized in admixtures with other additives, for example alkyl pyridinium halides, organic sulfates, organic sulfonates, the bisulfates illustrated in the copending applications mentioned herein, distearyl dimethyl ammonium methyl sulfate, and the like, generally there is present in the mixture an effective amount of each additive, such as for example from about 30 to about 80 percent by weight of the first additive of the present invention, and from about 20 to about 70 weight percent of the second charge additive in an embodiment of the present invention; from about 40 to about 60 percent by weight of the first additive of the present invention, and from about 60 to about 40 weight percent of the second charge additive in another embodiment of the present invention.

The following examples are being supplied to further define various species of the present invention, it being noted that these examples are intended to illustrate and not limit the scope of the present invention. Parts and percentages are by weight unless otherwise indicated.

EXAMPLE I

Chemical Synthesis of Distearyl Methyl Hydrogen Ammonium Bisulfate (DMHABS)

To 50 grams (93.5 millimol) of distearyl methyl amine (DMA, Armeen M218 available from Akzo Chemicals Company, melting point about 45° C.) was added 500 milliliters of methanol, and the resulting suspension in a 2 liter Buchner filter flask was gently heated to effect nearly complete solution with some residual haze. To this solution was cautiously added a solution of 50 milliliters of concentrated sulfuric acid ($H_2SO_4$, 900 millimol, 9.6 equivalents) in 200 milliliters of ice water then heated with stirring to 75° C. for about 30 minutes. The solution was cooled to room temperature to afford a white precipitate having a faint pink tint as a thick waxy solid. The solid was collected by filtration on a Whatman #4 paper with aspirator suction. The dried solid was recrystallized from methanol to afford, after air and vacuum drying, 47.6 grams (75 millimol, 80 percent theoretical yield) of the distearyl methyl hydrogen ammonium bisulfate (DMHABS) salt as a faint pink colored powder, melting point 120° to 145° C. with softening at about 95° C., and with slow decomposition, observed above 200° C. $^1$H NMR ($CDCl_3$) was δ9.35 (broad m, 1H, $HSO_4$), 4.2 (broad singlet, 1H, NH), 2.88 to 3.2 (multiplet containing a doublet, 7H, ($CH_3$)N and ($CH_2$)$_2$N), 1.74 (broad m, 4H, beta $CH_2$), 1.26 to 1.32 (m 30H, aliphatic $CH_2$), and 0.86 to 0.90 (t, 6H, aliphatic $CH_3$); IR(KBr) 1,011, 1,185, 1,471, 1,490 (shoulder), and 2,918.

EXAMPLE II

The DMHABS product of Example I was also prepared as follows. To 1,200 milliliters of ice water was cautiously added 250 milliliters of concentrated sulfuric acid ($H_2SO_4$), then the resulting mixture was stirred and allowed to thermally equilibrate at ambient temperature for about 2 hours. The aforementioned prepared aqueous $H_2SO_4$ solution was added to a suspension of 500 grams of DMA (0.94 mol) in 1,000 milliliters of water. The resulting suspension was mechanically stirred and heated on a hot plate (70° to 80° C.) in a 3 liter Buchner filter flask for 4 hours. The suspension was cooled to room temperature then filtered under reduced pressure overnight (18 hours) to remove the aqueous $H_2SO_4$. The water filtrate, aqueous $H_2SO_4$, was carefully neutralized with NaOH to a pH of about 7 before disposal. The retentate, an off-white, faint pink colored solid paste, was suspended in 2 liters of methanol with vigorous mixing then filtered under reduced pressure to remove additional water, $H_2SO_4$ and methanol soluble impurities. This filter cake was then suspended in 2 liters of hot methanol with vigorous mechanical stirring for about 30 minutes. The methanol suspension was cooled in an ice bath then filtered under reduced pressure to separate after drying about 450 grams (0.71 mol, 76 percent theoretical yield) of an off-white solid, m.p. 120° to 145° C. with softening at about 95° C., and with slow decomposition observed above 200° C. as in the above product DMHABS.

This procedure has an advantage, it is believed, in that it avoids having to hot filter/recrystallize the crude product as in Example I. Instead, this is accomplished by the methanol washing and reprecipitation steps.

EXAMPLE III

A solution of 25 grams (0.047 mol) of DMA in 200 milliliters of $CHCl_3$ was mixed with a solution of 15 milliliters of concentrated $H_2SO_4$ in 15 milliliters of water, and the mixture was heated with stirring for 3 hours. The reaction mixture was cooled to zero (0)° C. in an ice bath to separate a white precipitate which was collected by filtration. The crude material was recrystallized from acetone to afford 21 grams of the DMHABS product, identified in accordance with the procedure of Example I as a white powder, m.p. 120° to 145° C. with softening at about 95° C., and with slow decomposition observed above 200° C.

Also, the compounds prepared by the processes of Examples II and III were further identified by $^1$H NMR analysis and infrared (IR) analysis.

EXAMPLE IV

There was prepared in an extrusion device, available as ZSK28 from Werner Pfleiderer, a toner composition by adding thereto 80.13 percent by weight of suspension polymerized styrene butadiene copolymer resin particles (87/13), reference U.S. Pat. No. 4,558,108, the disclosure of which is totally incorporated herein by reference; 16.4 percent by weight of the magnetite Mapico Black; 3.15 percent by weight of Regal 330 ® carbon black; and 0.32 percent by weight of the charge enhancing additive distearyl methyl hydrogen ammonium bisulfate (DMHABS) obtained from Example II. The toner product which was extruded at a rate of 15 pounds per hour reached a melting temperature of 410° F. The strands of melt mixed product exiting from the extruder were cooled by immersing them in a water bath maintained at room temperature, about 25° C. Subsequent to air drying, the resulting toner was subjected to grinding in a Sturtevant micronizer enabling particles with a volume median diameter of from 8 to 12 microns as measured by a Coulter Counter. Thereafter, the aforementioned toner particles were classified in a Donaldson Model B classifier for the purpose of removing fine particles, that is those with a volume median diameter of less than 4 microns.

Subsequently, the above formulated toner, 3 parts by weight, was mixed with 97 parts by weight of a carrier containing a steel core with a polymer mixture thereof, 0.70 percent by weight, which polymer mixture contained 40 parts by weight of polyvinylidene fluoride, and 60 parts by weight of polymethyl methacrylate, and wherein mixing was accomplished in a paint shaker for 10 minutes. There resulted on the toner composition, as determined in the known Faraday Cage apparatus, a positive triboelectric charge of 19 microcoulombs per gram.

There was then added to the above prepared developer composition 1 part by weight of an uncharged toner prepared as above in the ZSK extruder as was the situation in the following Examples unless otherwise noted, comprised of 80.13 percent by weight of suspension polymerized styrene butadiene copolymer resin particles (87/13), reference U.S. Pat. No. 4,558,108, the disclosure of which is totally incorporated herein by reference; 16.4 percent by weight of the magnetite Mapico Black; 3.15 percent by weight of Regal 330 ® carbon black; and 0.32 percent by weight of the charge enhancing additive distearyl methyl hydrogen ammonium bisulfate of Example II. Thereafter, the charge distribution of the resulting developer was measured as a function of the mixing time, and it was determined by a charge spectrograph that the admixing time was less than 15 seconds, which was the shortest time that was measured on the known charge spectrograph for this added uncharged toner, that is this was the fastest admix that could be measured in this situation. This is also applicable to the examples that follow.

EXAMPLE V

There was prepared in an extrusion device, available as ZSK28 from Werner Pfleiderer, a toner composition by adding thereto 80.13 percent by weight of suspension polymerized styrene butadiene copolymer resin particles (87/13), reference U.S. Pat. No. 4,558,108, the disclosure of which is totally incorporated herein by reference; 16.4 percent by weight of the magnetite Mapico Black; 3.15 percent by weight of Regal 330 ® carbon black; and 0.32 percent by weight of the charge enhancing additive distearyl methyl hydrogen bisulfate (DMHABS) obtained from Example II. The toner was extruded at a rate of 6 pounds per hour and reached a temperature of 300° F. The toner strands of melt mixed product exiting from the extruder were cooled by immersion in a water bath by repeating the procedure of Example IV. Subsequently, the resulting toner was subjected to grinding in a Sturtevant micronizer enabling particles with a volume median diameter of from 8 to 12 microns as measured by a Coulter Counter. Thereafter, the aforementioned toner particles were classified in a Donaldson Model B classifier for the purpose of removing fine particles, that is those with a volume median diameter of less than 4 microns.

Subsequently, the above formulated toner, 3 parts by weight, was mixed with 97 parts by weight of a carrier containing a steel core with a polymer mixture thereof, 0.70 percent by weight, which polymer mixture contained 40 parts by weight of polyvinylidene fluoride and 60 parts by weight of polymethyl methacrylate, and wherein mixing was accomplished in a paint shaker for 10 minutes. There resulted on the toner composition, as determined in the known Faraday Cage apparatus, a positive triboelectric charge of 17 microcoulombs per gram.

There was then added to the above prepared developer composition 1 part by weight of an uncharged toner comprised of 80.13 percent by weight of suspension polymerized styrene butadiene copolymer resin particles (87/13), reference U.S. Pat. No. 4,558,108, the disclosure of which is totally incorporated herein by reference; 16.4 percent by weight of the magnetite Mapico Black; 3.15 percent by weight of Regal 330 ® carbon black; and 0.32 percent by weight of the charge enhancing additive distearyl methyl hydrogen ammonium bisulfate of Example II that is obtained by the process of Example II. Thereafter, the charge distribution of the resulting developer was measured as a function of the mixing time, and it was determined by a charge spectrograph that the admixing time was less than 15 seconds for the uncharged added toner determined in accordance with the procedure of Example IV.

EXAMPLE VI

There was prepared in an extrusion device, available as ZSK53 from Werner Pfleiderer, a toner composition by adding thereto 79.53 percent by weight of suspension polymerized styrene butadiene copolymer resin particles (87/13), reference U.S. Pat. No. 4,558,108, the disclosure of which is totally incorporated herein by reference; 17.0 percent by weight of the magnetite Mapico Black; 3.15 percent by weight of Regal 330 ® carbon black; and 0.32 percent by weight of the charge enhancing additive distearyl methyl hydrogen ammonium bisulfate (DMHABS) obtained from Example II. The toner was extruded at a rate of 275 pounds per hour with a temperature setting to achieve a melt temperature of 366° F. Thereafter, the toner product was cut into pellets with a knife, and cooled in a water bath by repeating the procedure of Example IV. Subsequently, the resulting toner was subjected to grinding in a Sturtevant micronizer enabling toner particles with a volume median diameter of from 8 to 12 microns as measured by a Coulter Counter. Thereafter, the aforementioned toner particles were classified in a Donaldson Model B classifier for the purpose of removing fine particles, that is those with a volume median diameter of less than 4 microns.

Subsequently, the above formulated toner, 3 parts by weight, was mixed with 97 parts by weight of a carrier containing a steel core with a polymer mixture thereof, 0.70 percent by weight, which polymer mixture contained 40 parts by weight of polyvinylidene fluoride and 60 parts by weight of polymethyl methacrylate, and wherein mixing was accomplished in a paint shaker for 10 minutes. There resulted on the toner composition, as determined in the known Faraday Cage apparatus, a positive triboelectric charge of 19 microcoulombs per gram.

There was then added to the above prepared developer composition 1 part by weight of a substantially uncharged toner comprised of 79.53 percent by weight of suspension polymerized styrene butadiene copolymer resin particles (87/13), reference U.S. Pat. No. 4,558,108, the disclosure of which is totally incorporated herein by reference; 17.0 percent by weight of the magnetite Mapico Black; 3.15 percent by weight of Regal 330 ® carbon black; and 0.32 percent by weight of the charge enhancing additive distearyl methyl hydrogen ammonium bisulfate obtained by the process of Example II. Thereafter, the charge distribution of the resulting developer was measured as a function of the mixing time, and it was determined by a charge spectrograph that the admixing time was less than 15 seconds for the added uncharged toner determined in accordance with the procedure of Example IV.

When a toner composition and developer composition are prepared by repeating the above procedures, and there is selected in place of the bisulfate charge enhancing additive, the known charge enhancing additive distearyl dimethyl ammonium methyl sulfate (DDAMS), the admix time for uncharged added toner was about 60 seconds.

EXAMPLE VII

There was prepared in an extrusion device, available as ZSK53 from Werner Pfleiderer, a toner composition by adding thereto 79.85 percent by weight of suspension polymerized styrene butadiene copolymer resin particles (87/13), reference U.S. Pat. No. 4,558,108, the disclosure of which is totally incorporated herein by reference; 17.0 percent by weight of the magnetite Mapico Black; 3.0 percent by weight of Regal 330 ® carbon black; and 0.15 percent by weight of the charge enhancing additive distearyl methyl hydrogen ammonium bisulfate by the process of Example II. The toner was extruded at a rate of 220 pounds per hour with temperature settings to achieve a melt temperature of 403° F. On exiting the extruder, the toner product was cut into pellets and cooled by repeating the procedure of Example IV. Subsequently, the toner was subjected to grinding in a Sturtevant micronizer enabling toner particles with a volume median diameter of from 8 to 12 microns as measured by a Coulter Counter. Thereafter, the aforementioned toner particles were classified in a Donaldson Model B classifier for the purpose of removing fine particles, that is those with a volume median diameter of less than 4 microns.

Subsequently, the above formulated toner, 3 parts by weight, was mixed with 97 parts by weight of a carrier containing a steel core with a polymer mixture thereof, 0.70 percent by weight, which polymer mixture contained 50 parts by weight of polyvinylidene fluoride, and 50 parts by weight of polymethyl methacrylate, and wherein mixing was accomplished in a paint shaker for 10 minutes. There resulted on the toner composition, as determined in the known Faraday Cage apparatus, a positive triboelectric charge of 17 microcoulombs per gram.

There was then added to the above prepared developer composition 1 part by weight of a toner comprised of 79.85 percent by weight of suspension polymerized styrene butadiene copolymer resin particles (87/13), reference U.S. Pat. No. 4,558,108, the disclosure of which is totally incorporated herein by reference; 17.0 percent by weight of the magnetite Mapico Black; 3.0 percent by weight of Regal 330 ® carbon black; and 0.15 percent by weight of the charge enhancing additive distearyl methyl hydrogen ammonium bisulfate of Example II. Thereafter, the charge distribution of the resulting developer was measured as a function of the mixing time, and it was determined by a charge spectrograph that the admixing time was less than 15 seconds for the added uncharged toner determined in accordance with the procedure of Example IV.

EXAMPLE VIII

About 10 of the 50 pounds of the toner prepared in Example VII, subsequent to cooling, was subjected to grinding in an Alpine Fluid Bed Jet Model 200 AFG, available from Hosokawa Micron International, enabling toner particles with a median diameter size of from 8 to 12 microns as measured by a Coulter Counter. Thereafter, the aforementioned toner particles were classified in a Donaldson Model B classified for the purpose of removing fine particles, that is those with a volume median diameter of less than 4 microns.

Subsequently, the above formulated toner, 3 parts by weight, was mixed with 97 parts by weight of a carrier containing a steel core with a polymer mixture thereof, 0.70 percent by weight, which polymer mixture contained 50 parts by weight of polyvinylidene fluoride and 50 parts by weight of polymethyl methacrylate, and wherein mixing was accomplished in a paint shaker for 10 minutes. There resulted on the toner composition, as determined in the known Faraday Cage apparatus, a positive triboelectric charge of 15 microcoulombs per gram.

This developer was then placed in a high speed electrostatic imaging machine available from Xerox Corporation as the 5090 TM and subsequent to engagement and development produced copies of high resolution with excellent solid areas of coverage, and substantially no background deposits under conditions of a toner dispense rate of about 30 grams per minute.

The admixing charging time of uncharged added toner comprised of the above components was substantially similar to that of Example VI, which admix time was determined by repeating the procedure of Example VI.

EXAMPLE IX

A slurry of 5.0 grams of Aerosil R972 (Degussa) in about 250 milliliters of the organic solvent methylene chloride were mixed thoroughly for 15 minutes in an explosion proof blender. The charge enhancing additive compound obtained by the process of Example II, namely distearyl methyl hydrogen ammonium bisulfate (0.5 gram) (DMHABS) was dissolved in 150 milliliters of additional methylene chloride solvent, followed by adding the resulting mixture to the aforementioned slurry of the Aerosil and methylene chloride. Mixing was accomplished for about 10 minutes. The resulting mixture was then transferred to a round-bottom flask surrounded by a water bath, which water bath was heated to about 40° C., and thereafter the mixture resulting in the flask was evaporated to dryness on a rotoevaporator. The residual solvent was then dried in a vacuum oven for 4 hours, then placed in a blender equipped with a 4 blade agitator, and fluffed to a powdery consistency. There resulted a fine powder comprised of Aerosil particles coated with the charge enhancing additive, distearyl methyl hydrogen ammonium bisulfate salt, with an average diameter of about 0.5 micron as determined by scanning electron microscopy.

EXAMPLE X

A black toner and developer composition was prepared by repeating the procedure of Example V with the exception that in place of the charge enhancing additive in the bulk there was selected 0.5 weight percent of the treated Aerosil articles of Example IX. More specifically, 50 grams, 99.5 weight percent, of the aforementioned toner, and 0.5 weight percent of the treated Aerosil particles of Example IX were placed in a paint shaker for 10 minutes and removed therefrom. A developer composition was then prepared by repeating the procedure of Example IV. The toner has a measured triboelectric charge of 25 microcoulombs per gram, and an admix time of 60 seconds for added uncharged toner, which admix was determined by the procedure of Example IV.

EXAMPLE XI

Cyan Developer

A cyan developer composition was prepared as follows: 45 parts by weight of a styrene butadiene resin (91/9), 45 parts by weight of styrene-n-butylmethacrylate resin and 7.5 parts by weight of Sudan Blue OS from BASF were melt blended at approximately 80° to 120° C. in an extruder, follwed by micronization and air classification to yield toner particles of a size of 9 microns in volume average diameter and 7 microns in number average diameter. The toner particles were then treated with the above prepared Aerosil treated charge control agent of Example IX by the addition thereof, 0.5 weight percent, and 99.5 weight percent of the above prepared cyan toner to a container with steel balls, and mixing thereof was accomplished for 30 minutes.

Subsequently, carrier particles were prepared by powder coating a Toniolo core, available from Toniolo Company, with a particle diameter range of from 80 to 150 microns with 0.7 parts by weight of a coating blend of 40 parts of Kynar and 60 parts of PMMA (polymethyl methacrylate) at 375° to 400° C. The magenta developer was then prepared by blending 97 parts by weight of the resulting coated carrier particles with 3 parts by weight of the above prepared toner in a lab blender for 10 minutes resulting in a developer composition.

The above prepared toner had a triboelectric charge of 42 microcoulombs per gram, and an admix time of 60 seconds, for added uncharged toner which characteristics were determined by the procedure of Example IV.

EXAMPLE XII

Magenta Developer

A magenta developer composition was prepared as follows: 90 parts by weight of a styrene butadiene resin (91/9), and 10 parts of a mixture of 5 parts Hostaperm Pink, available from American Hoechst, and 5 parts of styrene-n-butylmethacrylate were melt blended at approximately 80° to 120° C. in an extruder, followed by micronization and air classification to yield toner particles of an average particle diameter size of 9 microns in volume average diameter and 7 microns in number average diameter. The toner particles were then admixed with the Aerosil treated charge control agent of Example IX by repeating the procedure of Example XI.

Subsequently, carrier particles were prepared by powder coating a Toniolo core, available from Toniolo Company, with a particle diameter range of from 80 to 150 microns with 0.7 parts by weight of a coating blend of 40 parts of Kynar and 60 parts of PMMA (polymethyl methacrylate) at 375° to 400° C. The magenta developer was then prepared by blending 97 parts by weight of the aforementioned coated carrier particles with 3 parts by weight of the above prepared toner in a lab blender for 10 minutes resulting in a developer composition.

The above prepared toner had a triboelectric charge of 19 microcoulombs per gram, and an admix time of 0.5 minute, for added uncharged toner (in all instances unless otherwise noted this admix is for added uncharged toner) which characteristics were determined by the procedure of Example IV.

EXAMPLE XIII

Chemical Synthesis of Distearyl Dimethyl Ammonium Methyl Sulfonate (DDAMES) by Ionic Exchange To 500 milliliters of water was added 54 milliliters (80 grams, 0.83 mol, 3.7 eq.) of methane sulfonic acid, $CH_3SO_3H$ (available from Aldrich Chemical Compoany or Eastman Kodak Company). This solution, when cooled to room temperature, was added to a suspension of distearyl dimethyl ammonium methyl sulfate (DDAMS) (150.0 grams, 0.227 mol) suspended in 600 milliliters of water. The mixture was heated (70° to 80° C.) on a hot plate with stirring for 4 hours, cooled to room temperature and allowed to stand overnight. The mixture separated into an off-white/tan solid layer atop an aqueous layer. The mixture was filtered under reduced pressure and washed with water and air dried. The crude material was recrystallized from acetone and small amounts of methylene chloride. The methylene chloride appeared to help remove an unidentified waxy/sticky impurity to afford: 110 grams (0.17 mol), m.p. 70° C. (softening), 90° C. (liquid), and a second crop 13.7 grams (0.021 mol), m.p. 70° C. (softening), 87° C. (liquid) of the desired methane sulfonate salt (DDAMES).

Analysis Calculated for: $C_{38}H_{83}NSO_3$: C, 72.50; H, 12.98; N, 2.17; S, 4.95. Found: C, 71.66; H, 12.58; N, 2.22; S, 5.20.

EXAMPLE XIV

Chemical Synthesis of Distearyl Dimethyl Ammonium Trifluoromethyl Sulfonate (DDATRIF) by Ionic Exchange To 500 milliliters of water was cautiously added 43 milliliters (72.9 grams, 0.486 mol) of trifluoromethane sulfonic acid, $CF_3SO_3H$ (3M Corporation, Fluorad FC-24, anhydrous). This solution was cooled to room temperature then added to a suspension of distearyl dimethyl ammonium methyl sulfate (DDAMS) (150 grams, 0.227 mol) in 600 milliliters water. The mixture was heated on a hot plate with stirring (80° to 90° C.) for 4 hours, cooled to room temperature and allowed to stand overnight (16 hours). The mixture had separated into a tan solid layer atop the aqueous layer. The solid layer was broken up and the aqueous phase removed by filtration under reduced pressure. The tan solid was washed with water then air dried for 1 hour. The crude material was recrystallized from acetone to afford 114.7 grams (0.164 mol, 72 percent theory), m.p. 90° C. (soften), 119° C. (liquid) of the above trifluoromethane sulfonate salt (DDATRIF), as an off-white powder. A second crop, 17 grams of a tan-yellow solid, was unacceptable for use without further extensive purification.

Analysis Calculated for: $C_{39}H_{80}NSO_3F_3$: C, 66.92; H, 11.54; N, 2.00; S, 4.57. Found: C, 66.76; H, 11.32; N, 2.17; S, 5.01.

EXAMPLE XV

DDAMES Black Developer

There was prepared in an extrusion device, available as ZSK28 from Werner Pfleiderer, a toner composition by adding thereto 80.13 percent by weight of suspension polymerized styrene butadiene copolymer resin particles (87/13); 16.4 percent by weight of the magnetite Mapico Black; 3.15 percent by weight of Regal 330 ® carbon black; and 0.32 percent by weight of the charge enhancing additive distearyl dimethyl ammonium methyl sulfonate (DDAMES) obtained from Example XIII. The toner product which was extruded at a rate of 15 pounds per hour reached a melting temperature of 410° F. The strands of melt mixed product exiting from the extruder were cooled by immersing them in a water bath maintained at room temperature, about 25° C. Subsequent to air drying, the resulting toner was subjected to grinding in a Sturtevant micronizer enabling particles with a volume median diameter of from 8 to 12 microns as measured by a Coulter Counter. Thereafter, the aforementioned toner particles were classified in a Donaldson Model B classifier for the purpose of removing fine particles, that is those with a volume median diameter of less than 4 microns.

Subsequently, the above formulated toner, 3 parts by weight, was mixed with 97 parts by weight of the carrier composition of Example VIII, and wherein mixing was accomplished in a paint shaker for 10 minutes. There resulted on the toner composition, as determined in the known Faraday Cage apparatus, a positive triboelectric charge of 24 microcoulombs per gram.

There was then added to the above prepared developer composition 1 part by weight of an uncharged toner comprised of 80.13 percent by weight of suspension polymerized styrene butadiene copolymer resin particles (87/13), reference U.S. Pat. No. 4,558,108; 16.4 percent by weight of the magnetite Mapico Black; 3.15 percent by weight of Regal 330 ® carbon black; 0.32 percent by weight of the charge enhancing additive distearyl dimethyl ammonium methyl sulfonate (DDAMES) of Example XIII. Thereafter, the charge distribution of the resulting developer was measured as a function of the mixing time, and it was determined by a charge spectrograph that the admixing time was less than 15 seconds, or added uncharged toner.

EXAMPLE XVI

DDATRIF Black Developer

There was prepared in an extrusion device, available as ZSK28 from Werner Pfleiderer, a toner composition by adding thereto 80.13 percent by weight of suspension polymerized styrene butadiene copolymer resin particles (87/13), reference U.S. Pat. No. 4,558,108, the disclosure of which is totally incorporated herein by reference; 16.4 percent by weight of the magnetite Mapico Black; 3.15 percent by weight of Regal 330 ® carbon black; and 0.32 percent by weight of the charge enhancing additive distearyl dimethyl ammonium trifluoromethyl sulfonate (DDATRIF) obtained from Example XIV. The toner product, which was extruded at a rate of 15 pounds per hour, reached a melting temperature of 410° F. The strands of melt mixed product exiting from the extruder were cooled by immersing them in a water bath maintained at room temperature, about 25° C. Subsequent to air drying, the resulting toner was subjected to grinding in a Sturtevant micronizer enabling particles with a volume median diameter of from 8 to 12 microns as measured by a Coulter Counter. Thereafter, the aforementioned toner particles were classified in a Donaldson Model B classifier for the purpose of removing fine particles, that is those with a volume median diameter of less than 4 microns.

Subsequently, the above formulated toner, 3 parts by weight, was mixed with 97 parts by weight of the carrier composition of Example VIII, and wherein mixing was accomplished in a paint shaker for 10 minutes. There resulted on the toner composition, as determined in the known Faraday Cage apparatus, a positive triboelectric charge of 24 microcoulombs per gram.

There was then added to the above prepared developer composition 1 part by weight of an uncharged toner comprised of 80.13 percent by weight of suspension polymerized styrene butadiene copolymer resin particles (87/13), reference U.S. Pat. No. 4,558,108; 16.4 percent by weight of the magnetite Mapico Black; 3.15 percent by weight of Regal 330 ® carbon black; 0.32 percent by weight of the charge enhancing additive distearyl dimethyl ammonium trifluoromethyl sulfonate (DDATRIF) obtained from Example XIV. Thereafter, the charge distribution of the resulting developer was measured as a function of the mixing time, and it was determined by a charge spectrograph that the admixing time was less than 15 seconds.

EXAMPLE XVII

DDAMES Magenta Developer

A magenta developer composition was prepared as follows: 90 parts by weight of a styrene butadiene resin (91/9), and 10 parts of a mixture of 5 parts Hostaperm Pink E, available from American Hoechst, and 5 parts of styrene-n-butylmethacrylate were melt blended at approximately 80° to 120° C. in an extruder, followed by micronization and air classification to yield toner particles of an average particle diameter size of 9 microns in volume average diameter and 7 microns in number average diameter. The toner particles were then admixed with the Aerosil particles treated with the distearyl dimethyl ammonium methyl sulfonate (DDAMES) charge control agent of Example XIII, prepared analogously to the treated Aerosil of Example IX and therein repeating the toner and Aerosil blending procedure described in Example XI.

Subsequently, carrier particles were prepared by powder coating a Toniolo core, available from Toniolo Company, with a particle diameter range of from 80 to 150 microns with 0.7 parts by weight of a coating blend of 40 parts of Kynar and 60 parts of PMMA (polymethyl methacrylate) at 375° to 400° C. The magenta developer was then prepared by blending 97 parts by weight of the aforementioned coated carrier particles with 3 parts by weight of the above prepared toner in a lab blender for 10 minutes resulting in a developer composition.

The above prepared toner had a triboelectric charge of 59 microcoulombs per gram, and an admix time of less than 30 seconds, which characteristics were determined by the procedure of Example IV. A control toner, that is a magenta toner composition with Aerosil untreated with DDAMES had an admix time of greater than 15 minutes.

EXAMPLE XVIII

DDATRIF Magenta Developer

A magenta developer composition was prepared as follows: 90 parts by weight of a styrene butadiene resin (91/9), and 10 parts of a mixture of 5 parts Hostaperm Pink E, available from American Hoechst, and 5 parts of styrene-n-butylmethacrylate were melt blended at approximately 80° to 120° C. in an extruder, followed by micronization and air classification to yield toner particles of an average particle diameter size of 9 microns in volume average diameter and 7 microns in number average diameter. The toner particles were then admixed with the Aerosil particles treated with the distearyl dimethyl ammonium trifluoromethyl sulfonate_(DDATRIF) charge control agent of Example XIV, prepared analogously to the treated Aerosil of Example IX, and therein repeating the toner and Aerosil blending procedure described in Example XI.

Subsequently, carrier particles were prepared by powder coating a Toniolo core, available from Toniolo Company, with a particle diameter range of from 80 to 150 microns with 0.7 parts by weight of a coating blend of 40 parts of Kynar and 60 parts of PMMA (polymethyl methacrylate) at 375° to 400° C. The magenta developer was then prepared by blending 97 parts by weight of the aforementioned coated carrier particles with 3 parts by weight of the above prepared toner in a lab blender for 10 minutes resulting in a developer composition.

The above prepared toner had a triboelectric charge of 55 microcoulombs per gram, and an admix time of less than 30 seconds, which characteristics were determined by the procedure of Example IV. A control toner, that is a magenta toner composition with Aerosil untreated with DDATRIF had an admix time of greater than 15 minutes.

In the above Examples, all the admix times were determined in a known charge spectrograph.

Other modifications of the present invention may occur to those skilled in the art subsequent to a review of the present application, and these modifications, including equivalents thereof, are intended to be included within the scope of the present invention.

What is claimed is:

1. A toner composition comprised of resin particles, pigment particles, and a quaternary ammonium hydrogen bisulfate charge enhancing additive.

2. A method of imaging which comprises formulating an electrostatic latent image on a photoreceptor, affecting development thereof with the toner composition of claim 1, and thereafter transferring the developed image to a suitable substrate.

3. A method of imaging in accordance with claim 2 wherein the transferred image is permanently fixed to the substrate.

4. A toner composition comprised of resin particles, pigment particles, and a quaternary ammonium hydrogen bisulfate charge enhancing additive of the formula $R'_2N+R''HX-$, wherein $R'$ is alkyl or aryl, $R''$ is alkyl or aryl, and X is a bisulfate anion.

5. A toner composition in accordance with claim 2 wherein the charge enhancing additive is selected form the group consisting of distearyl methyl hydrogen ammonium bisulfate, didodecyl methyl ammonium hydrogen bisulfate, dihexadecyl methyl ammonium hydrogen bisulfate, distearyl ethyl ammonium hydrogen bisulfate, and bis(distearyl methyl hydrogen ammonium) sulfate.

6. A toner composition in accordance with claim 4 wherein the charge additive is present in an amount of from about 0.05 to about 5 weight percent.

7. A toner composition in accordance with claim 4 wherein the charge additive is present in an amount of from about 0.1 to about 3 weight percent.

8. A toner composition in accordance with claim 4 wherein the charge additive is incorporated into the toner.

9. A toner composition in accordance with claim 4 wherein the charge additive is present on the surface of the toner composition.

10. A toner composition in accordance with claim 9 wherein the charge additive is contained on colloidal silica particles.

11. A toner composition in accordance with claim 4 with an admix time of from less than about 15 seconds.

12. A toner composition in accordance with claim 4 with an admix time of from about 1 to about 14 seconds.

13. A toner composition in accordance with claim 4 with a triboelectric charge of from about 10 to about 40 microcoulombs per gram.

14. A toner composition in accordance with claim 4 wherein a colloidal silica is treated with the charge enhancing additive, and the resulting composition is present on the surface of the toner.

15. A toner composition in accordance with claim 4 wherein the resin particles are comprised of styrene polymers, polyesters, or mixtures thereof.

16. A toner composition in accordance with claim 4 wherein the resin particles are comprised of styrene acrylates, styrene methacrylates, or styrene butadienes.

17. A toner composition in accordance with claim 4 containing a wax component with a weight average molecular weight of from about 1,000 to about 6,000.

18. A toner composition in accordance with claim 17 wherein the waxy component is selected from the group consisting of polyethylene and polypropylene.

19. A toner composition in accordance with claim 4 containing as external additives metal salts of a fatty acid, colloidal silicas, or mixtures thereof.

20. A toner composition in accordance with claim 4 wherein the pigment particles are carbon black, magnetites, or mixtures thereof, cyan, magenta, yellow, red, blue, green, brown, and mixtures thereof.

21. A developer composition comprised of the toner composition of claim 4 and carrier particles.

22. A developer composition in accordance with claim 21 wherein the carrier particles are comprised of ferrites, steel, or an iron powder.

23. A developer composition in accordance with claim 21 wherein the carrier particles are comprised of a core with a polymer coating thereover.

24. A developer composition in accordance with claim 23 wherein the coating is comprised of a methyl terpolymer, a polyvinylidine fluoride, a polymethyl methacrylate, or a mixture of polymers not in close proximity in the triboelectric series.

25. A method of imaging which comprises formulating an electrostatic latent image on a negatively charged photoreceptor, affecting development thereof with the toner composition of claim 4, and thereafter transferring the developed image to a suitable substrate.

26. A method of imaging in accordance with claim 25 wherein the transferred image is permanently fixed to the substrate.

27. A toner composition in accordance with claim 4 wherein the charge enhancing additive is stable at high temperatures.

28. A toner composition in accordance with claim 27 wherein the charge enhancing additive is stable at temperatures of from about 130° to about 160° C.

29. A toner in accordance with claim 4 wherein $R'$ is alkyl with from 1 to about 25 carbon atoms.

30. A toner in accordance with claim 29 wherein $R''$ is alkyl with from 1 to about 8 carbon atoms.

31. A toner comprised of resin, pigment, and the charge additive of claim 4.

32. A toner composition comprised of resin particles, pigment particles, and a quaternary ammonium hydrogen bisulfate charge enhancing additive of the formula $R_3NH + HSO_4-$, wherein R is alkyl.

33. A toner composition in accordance with claim 32 wherein the charge additive is present in an amount of from about 0.1 to about 3 weight percent.

34. A toner composition comprised of resin particles, pigment particles and a charge enhancing additive selected from the group consisting of distearyl dimethyl ammonium methyl sulfonate, distearyl dimethyl ammonium trifluoromethyl sulfonate, didodecyl dimethyl ammonium methyl sulfonate, dihexadecyl dimethyl ammonium methyl sulfonate, didodecyl methyl ammonium methyl sulfonate, dihexadecyl methyl ammonium hydrogen trifluoromethyl sulfonate, distearyl diethyl ammonium ethyl sulfonate, distearyl methyl ammonium hydrogen methyl sulfate, distearyl dimethyl ammonium perfluoroethyl sulfonate, and distearyl diethyl ammonium perfluoroethyl sulfonate.

35. A single component positively charged toner composition comprised of resin particles, magnetite components, and a quaternary ammonium hydrogen bisulfate charge enhancing additive of the formula $R'_2N + R''HX-$, wherein R is alkyl with from 1 to about 25 carbon atoms or aryl, $R''$ is alkyl with from 1 to about 8 carbon atoms or aryl, and X is a bisulfate anion.

36. A toner comprised of resin, pigment, and a quaternary ammonium hydrogen bisulfate charge additive.

* * * * *